(12) United States Patent
Petschke et al.

(10) Patent No.: US 9,256,938 B2
(45) Date of Patent: Feb. 9, 2016

(54) CHARACTERISTIC X-RAY ESCAPE CORRECTION IN PHOTON-COUNTING DETECTORS

(71) Applicants: KABUSHIKI KAISHA TOSHIBA, Minato-ku (JP); Toshiba Medical Systems Corporation, Otawara-shi (JP)

(72) Inventors: Adam Petschke, Lake Bluff, IL (US); Yu Zou, Naperville, IL (US)

(73) Assignees: KABUSHIKI KAISHA TOSHIBA, Minato-ku (JP); TOSHIBA MEDICAL SYSTEMS CORPORATION, Otawara-shi (JP)

( * ) Notice: Subject to any disclaimer, the term of this patent is extended or adjusted under 35 U.S.C. 154(b) by 54 days.

(21) Appl. No.: 14/190,170

(22) Filed: Feb. 26, 2014

(65) Prior Publication Data

US 2015/0243022 A1     Aug. 27, 2015

(51) Int. Cl.
*G06K 9/00* (2006.01)
*G06T 7/00* (2006.01)
*G06T 5/00* (2006.01)
*G06K 9/52* (2006.01)

(52) U.S. Cl.
CPC ............... *G06T 7/0012* (2013.01); *G06K 9/52* (2013.01); *G06T 5/00* (2013.01); *G06T 2207/10081* (2013.01); *G06T 2207/10116* (2013.01)

(58) Field of Classification Search
CPC .......... G06K 9/00; G06K 9/52; G06T 7/0012; G06T 5/00; G06T 2207/10081; G06T 2207/10116
USPC ......................................................... 382/131
See application file for complete search history.

(56) References Cited

U.S. PATENT DOCUMENTS

| | | | | |
|---|---|---|---|---|
| 2010/0027743 | A1* | 2/2010 | Engel | G01T 1/1647 378/62 |
| 2012/0326049 | A1* | 12/2012 | Hannemann | G01T 1/243 250/394 |
| 2013/0099127 | A1* | 4/2013 | Atzinger | G01T 1/2928 250/371 |
| 2013/0304409 | A1* | 11/2013 | Beaulieu | G01T 7/005 702/104 |

* cited by examiner

*Primary Examiner* — Gregory F Cunningham
(74) *Attorney, Agent, or Firm* — Oblon, McClelland, Maier & Neustadt, L.L.P.

(57) ABSTRACT

A method and an apparatus for determining primary and secondary escape probabilities for a large photon-counting detector without pile-up. A model for the detector with no pile-up is formulated and used for spectrum correction in a computed tomography scanner. The method includes computing primary K-escape and secondary K-escape probabilities occurring at a certain depth within the photon-counting detector. Further, a no pile-up model for the photon-counting detector is formulated by determining a response function, based on the computed primary and secondary K-escape probabilities and geometry of the photon-counting detector. The method includes obtaining a measured CT scan of an object and further performs spectrum correction by determining the incident input spectrum based on the response function and the measured spectrum of the large photon-counting detector.

17 Claims, 6 Drawing Sheets

CHARACTERISTIC X-RAY ESCAPE CORRECTION IN PHOTON-COUNTING DETECTORS

FIELD

Embodiments disclosed herein generally relate to computed tomography (CT) imaging. In particular, embodiments disclosed herein relate to a CT apparatus including a plurality of photon-counting detectors and an associated method thereof for performing spectrum correction that incorporates the phenomenon of characteristic X-ray escape from the photon-counting detectors.

BACKGROUND

When high energy photons impinge on a detector, the inner shell electrons from atoms of the detector are ejected from the atom as "photoelectrons." This phenomenon leaves the atom in an excited state with a vacancy (hole) in the inner electron shell. Outer shell electrons then fall into the created holes, thereby emitting photons with energy equal to the energy difference between the two states. Since each element has a unique set of energy levels, each element emits a pattern of X-rays characteristic of the element, termed "characteristic X-rays." The intensity of the X-rays increases with the concentration of the corresponding element.

In many materials such as Cadmium Telluride (CdTe) or Cadmium Zinc Telluride (CZT) or the like, the characteristic X-rays primarily involve K-shell (closest shell to the nucleus of an atom) electrons. If the characteristic X-rays escape from the detector, the detector signal is incorrect and the loss of energy incurred manifests itself as errors in the output spectrum of the detectors. Thus, the measured spectral signal can be distorted and may cause artifacts in the reconstructed image.

The phenomenon of characteristic X-ray escape from the semiconductor detectors and the corresponding spectrum correction can be modeled using a Monte Carlo simulation. However, Monte Carlo simulations rely on random sampling in order to obtain numerical results in a heuristic manner, and thus tend to be computationally intensive. Accordingly, accurate image reconstruction can be achieved in real time by analytically modelling the characteristic X-ray escape phenomenon and correcting the measured output spectrum.

BRIEF DESCRIPTION OF THE DRAWINGS

A more complete appreciation of the disclosed embodiments and many of the attendant advantages thereof will be readily obtained as the same becomes better understood by reference to the following detailed description when considered in connection with the accompanying drawings, wherein.

DETAILED DESCRIPTION

Figure 1:
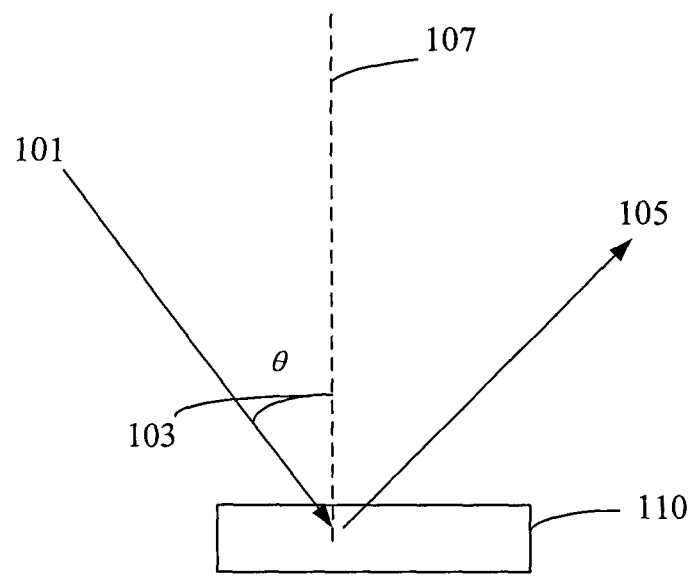
FIG. 1 illustrates a phenomenon of characteristic X-ray escape from a photon-counting detector.

Embodiments disclosed herein relate to an apparatus and method for performing spectrum correction. Specifically, embodiments described herein relate to a method and an apparatus for determining primary escape probability and secondary escape probability for a large photon-counting detector with no pile-up. For large photon counting detectors, the ratio of energy that escapes from the top surface of the detector to the amount of energy that escapes from the sides of the detector is large. In such cases, an analytical model described herein can be used to compute the escape probabilities and perform spectrum correction. For detectors of a smaller size, Monte Carlo simulations can be used to determine the probabilities of escape from the surfaces of the detector.

According to one embodiment, a method of performing no-pileup correction for a spectral computed-tomography scanner, the scanner including a large photon-counting detector, the method includes: computing a primary K-escape probability and a secondary K-escape probability for the photon-counting detector; determining a response function for the photon-counting detector based on the computed primary and secondary K-escape probabilities and a geometry of the photon counting detector; obtaining a measured output spectrum of an object; and performing the spectrum correction by determining, using the response function and the measured output spectrum, an incident spectrum for the photon-counting detector.

According to another embodiment is provided a computed-tomography (CT) apparatus for performing spectrum correction, the apparatus comprising: a photon counting detector configured to capture incident X-ray photons emitted from an X-ray source; and processing circuitry configured to compute a primary K-escape probability and a secondary K-escape probability for the photon-counting detector; determine a response function for the photon-counting detector based on the computed primary and secondary K-escape probabilities and a geometry of the photon counting detector; obtain CT data corresponding to a measured output spectrum of an object; and perform the spectrum correction by determining, using the response function and the measured output spectrum, an incident spectrum for the photon-counting detector.

In another embodiment of the disclosure is provided a non-transitory computer readable medium having stored thereon a program that when executed by a computer, causes the computer to execute a method, the method includes the steps of: computing a primary K-escape probability and a secondary K-escape probability for the photon-counting detector; determining a response function for the photon-counting detector based on the computed primary and secondary K-escape probabilities and a geometry of the photon counting detector; obtaining a measured output spectrum of an object; and performing the spectrum correction by determining, using the response function and the measured output spectrum, an incident spectrum for the photon-counting detector.

Turning to FIG. 1, a phenomenon of characteristic X-ray escape from a single photon-counting detector is illustrated. In FIG. 1, an incident photon 101 impinges the surface of a detector 110 at an incident angle 103, represented as θ. The incident angle θ is the angle formed between the incident beam 101 and a normal 107 to the surface of the detector. Upon photoelectrical interaction in the detector 110, a photon 105 escapes from the detector. Specifically, the photoelectric effect occurs when the detector emits electrons upon absorbing radiation such as X-rays.

Upon occurrence of a photoelectrical effect, the number of counts (photons) measured at each energy level is not the same as the incident number of photon counts. For instance, if an incident photon at 100 keV (kilo-electron volts) has a photoelectrical interaction in the detector and a 30 keV photon escapes in the process, the photon energy recorded is 70 keV. Thus, the number of counts measured at 100 keV is lower than the actual counts occurring at 100 keV and the number of counts measured at 70 keV is higher than the actual counts occurring at 70 keV.

The probability of escape increases as the incident angle 103 increases, as the photoelectric interaction occurs closer to the surface of the detector. Furthermore, in a pixelated detector, a photon that escapes from one pixel may interact with a neighboring pixel, thereby distorting the spectrum of both pixels. Accordingly, the present disclosure provides for analytical models to compute the different K-escape probabilities of the photon-counting detectors, and further correct the measured spectrum of the photon-counting detectors based on the computed probabilities.

One embodiment provides for correction of primary escape in photon-counting detectors. In the present embodiment, it is assumed that the characteristic X-rays that escape from a detector are not reabsorbed by a neighboring detector.

The primary K-escape probability, $P_p(E_0, z_0)$, of a large detector without secondary absorption and emission can be defined as:

$$P_p(E_0, z_0) = \sum_n P_n(E_0) \frac{1}{4\pi} \int_0^{2\pi} d\varphi \int_0^{\frac{\pi}{2}} d\theta \sin\theta e^{-\frac{\mu_n z_0}{\cos\theta}}, \quad (1)$$

wherein $E_0$ is the energy of the incident photon, $z_0$ is the depth of photon interaction, n is summed over all K edges (i.e., n is a variable that corresponds to the different types of escapes, each having a corresponding level of energy), $P_n(E_0)$ is the probability of a K-edge photon being emitted given that a photoelectric interaction has occurred, $\varphi$ is the azimuthal angle of the emitted edge photon, $\theta$ is the polar angle of the emitted K-edge photon, and $\mu_n$ is the attenuation coefficient of the detector at the K-edge energy.

Upon integrating over the azimuthal angle, the primary K-escape probability can be expressed as:

$$P_p(E_0, z_0) = \sum_n \frac{P_n(E_0)}{2} \int_0^{\frac{\pi}{2}} d\theta \sin\theta e^{-\frac{\mu_n z_0}{\cos\theta}}. \quad (2)$$

Equation (2) can be simplified by defining $\cos\theta = u^{-1}$ which gives $$P_p(E_0, z_0) = \sum_n \frac{P_n(E_0)}{2} \int_1^\infty du \frac{e^{-\mu_n z_0 u}}{u^2}. \quad (3)$$

Equation (3) can be integrated over the variable u to produce:

$$P_p(E_0, z_0) = \sum_n \frac{P_n(E_0)}{2} (\mu_n z_0 Ei(-\mu_n z_0) + e^{-\mu_n z_0}), \quad (4)$$

wherein, $$Ei(x) = P\int_{-\infty}^x dt \frac{e^t}{t} = \gamma + \ln|x| + \sum_{k=1}^\infty \frac{x^k}{kk!}$$

is the exponential integral with P denoting a principal value and $\gamma \approx 0.577$ is Euler's constant.

Having evaluated the primary K-escape probability, as shown in equations (2)-(4), the measured component spec trum without pileup (event that contains a single photon in a photoelectric effect) can be modeled as:

$$S_0(E) = \chi_0 e^{-N\tau_d} \quad (5)$$

$$\int\int dz_0 dE_0 S_{in}(E_0)[1 - P(E_0, z_0)] e^{-\mu_{CZT}(E_0) z_0 / \sin\beta} \frac{\mu_{CZT}(E_0)}{\sin\beta} +$$

$$\chi_0 e^{-N\tau_d} \sum_n \int\int dz_0 dE_0 S_{in}(E_0 + \Delta_n) P_n(E_0 + \Delta_n, z_0)$$

$$e^{-\mu_{CZT}(E_0 + \Delta_n) z_0} \frac{\mu_{CZT}(E_0 + \Delta_n)}{\sin\beta},$$

wherein $S_0(E)$ is the measured component spectrum without pileup, $\chi_0$ is the detection probability (for the case of no-pile up, the parameter $\chi_0 = 1$), N is the incident flux, $\tau_d$ is the dead time of the detector, $z_0$ is a depth within the photon-counting detector at which the photoelectric interaction occurs, $E_0$ is the energy that fulfils the energy condition determined by detector geometry and electronics, $S_{in}$ is the incident spectrum, $P(E_0, z_0)$ is the total probability of escape (i.e., $P(E_0, z_0)$ is equal to the primary K-escape probability $P_p(E_0, z_0)$), $\mu_{CZT}$ is the attenuation coefficient, $\beta$ is the incident photon angle, n is a parameter that sums the different ways of escape from materials having different energy levels, $\Delta_n$ is the escape energy, and $P_n$ are the different escape probabilities.

The primary K-escape of Cd (n=1) can be determined as follows:

$$P_1(E_0 + \Delta_1, z_0) = \frac{P_1(E_0)}{2}(\mu_1 z_0 Ei(-\mu_1 z_0) + e^{-\mu_1 z_0}) \quad (6)$$

The primary K-escape of Te (n=2) can be determined as follows:

$$P_2(E_0 + \Delta_2, z_0) = \frac{P_2(E_0)}{2}(\mu_2 z_0 Ei(-\mu_2 z_0) + e^{-\mu_2 z_0}) \quad (7)$$

Note that the summation over n includes the $K_\alpha$ emission of Cd and the $K_\alpha$ of emission of Te. With regard to equation (5), the measured signal includes a contribution in part by an absorbed photon that deposits energy into the detector. Specifically, the energy deposited can either stay in the detector and contribute to the measured signal, or the energy can escape (K-escape) from the detector. The first term in equation (5) is the contribution to the measured spectrum for cases when there is no K-escape. The second term in equation (5) is the contribution to the measured signal when there is a K-escape. Specifically, even when there is K-escape, not all of the energy associated with the K-escape leaves the detector. A part of the K-escape energy contributes towards the measured spectrum.

Figure 2:
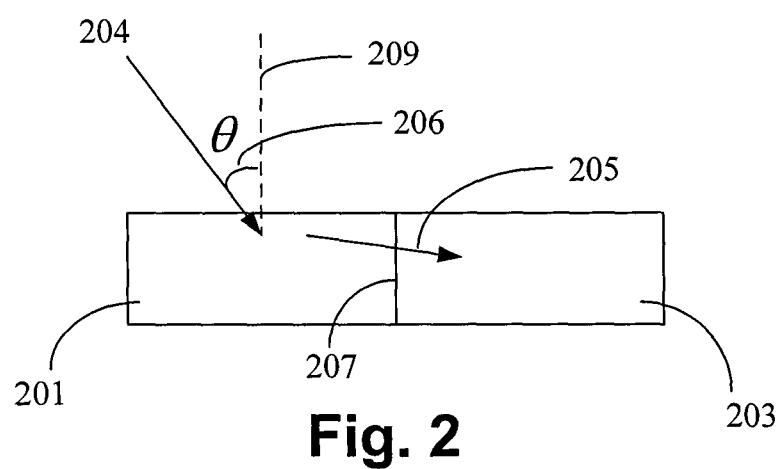
FIG. 2 illustrates, according to an embodiment, a phenomenon of characteristic X-ray escape and secondary emission.

FIG. 2 illustrates a phenomenon of characteristic X-ray escape and secondary emission occurring in photon-counting detectors according to one embodiment. In FIG. 2, elements 201 and 203 are detectors that share a neighboring edge 207. An incident photon beam 204 impinges the detector 201 at an incident angle $\theta$, represented as 206. The incident angle $\theta$ is the angle formed between the incident beam 204 and a normal 209 to the surface of the detector 201.

In the present embodiments, upon the occurrence of a photoelectric interaction of the incident photon 204 in the detector 201, the resulting emission escapes through the neighboring edge 207 into the adjacent detector 203, as shown by the beam 205. Thus, the emission is absorbed by the neighboring detector 203, which causes a secondary emission from the detector 203. The process of a first emission followed by absorption and a secondary emission can be represented as:

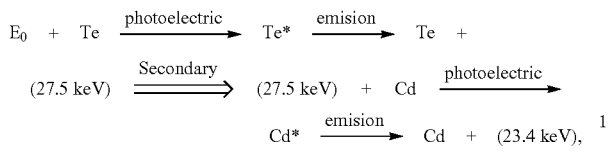

wherein Te* and Cd* indicate the excited state of Te and Cd atoms where a K-shell hole exists.

In the present embodiments, the measured output spectrum can be represented as:

$$S_0(E) = \chi_0 e^{-N\tau_d} \quad (8)$$

$$\int\int dz_0 dE_0 S_{in}(E_0)[1-P(E_0,z_0)]e^{-\mu_{CZT}(E_0)z_0/\sin\beta}\frac{\mu_{CZT}(E_0)}{\sin\beta}+$$

$$\chi_0 e^{-N\tau_d}\sum_n \int\int dz_0 dE_0 S_{in}(E_0+\Delta_n)P_n(E_0+\Delta_n,z_0)$$

$$e^{-\mu_{CZT}(E_0+\Delta_n)z_0}\frac{\mu_{CZT}(E_0+\Delta_n)}{\sin\beta}$$

Equation (8) is similar to equation (5). However, the term $P(E_0, z_0)$, which represents the total probability of escape, includes a primary probability of escape and a secondary probability of escape. Specifically, $P(E_0, z_0) = P_p(E_0, z_0) + P_s(E_0, z_0)$. The probability of primary escape $P_p(E_0, z_0)$, can be computed as described in equations (1) to (4). The secondary probability of escape of a large detector can be computed as follows:

$$P_s(E_0, z_0) = \quad (9)$$

$$\frac{P_1(E_0)P_{21}\mu_1}{(4\pi)^2}\int_0^{2\pi}\int_0^{2\pi}\int_0^{\frac{\pi}{2}}\int_0^{\frac{\pi}{2}}\int_0^{z_0} d\varphi d\varphi' d\theta d\theta' dz \frac{\sin\theta}{\cos\theta}\sin$$

$$\theta' e^{-\frac{\mu_1(z_0-z)}{\cos\theta}}e^{-\frac{\mu_2 z}{\cos\theta'}} - \frac{P_1(E_0)P_{21}\mu_1}{(4\pi)^2}$$

$$\int_0^{2\pi}\int_0^{2\pi}\int_{\frac{\pi}{2}}^{\pi}\int_0^{\frac{\pi}{2}}\int_{z_0}^{\infty} d\varphi d\varphi' d\theta d\theta' dz \frac{\sin\theta}{\cos\theta}\sin\theta' e^{-\frac{\mu_1(z_0-z)}{\cos\theta}}e^{-\frac{\mu_2 z}{\cos\theta'}},$$

where $E_0$ is the energy of the incident photon, $z_0$ is the depth in the detector at which the primary photon interaction occurs, $P_1(E_0)$ is the probability of a K-edge photon being emitted at a higher energy K edge given a photoelectric interaction has occurred from the incident photon energy $E_0$, $P_{21}$ is the probability of a K-edge photon being emitted from a lower-energy K-edge given that a photoelectric interaction has occurred from the higher energy K-edge, $\mu_n$ is the attenuation coefficient of the detector at each K-edge energy, $\varphi$ and $\varphi'$ are the azimuthal angles of the primary and secondary emitted photons, respectively, $\theta$ and $\theta'$ are the polar angles of the primary and secondary emitted photons, and z is the depth of the secondary photon interaction.

Upon performing an integration operation over the variables $\varphi$ and $\varphi'$ and defining $\cos\theta = u^{-1}$ and $\cos\theta' = v^{-1}$ the secondary escape probability can be expressed as:

$$P_s(E_0, z_0) = \frac{P_1(E_0)P_{21}\mu_1}{4}\int_1^\infty\int_1^\infty\int_0^{z_0}\frac{du}{u}\frac{dv}{v^2}dz e^{-\mu_1(z_0-z)u}e^{-\mu_2 zv}+ \quad (10)$$

$$\frac{P_1(E_0)P_{21}\mu_1}{4}\int_1^\infty\int_1^\infty\int_{z_0}^\infty \frac{du}{u}\frac{dv}{v}dz e^{\mu_1(z_0-z)u}e^{-\mu_2 zv}.$$

$$P_s(E_0, z_0) = \quad (11)$$

$$-\frac{P_1(E_0)P_{21}\mu_1}{4}\int_0^{z_0} dz(\mu_2 z Ei(-\mu_2 z)+e^{-\mu_2 z})Ei(-\mu_1(z_0-z))-$$

$$\frac{P_1(E_0)P_{21}\mu_1}{4}\int_{z_0}^\infty dz(\mu_2 z Ei(-\mu_2 z)+e^{-\mu_2 z})Ei(\mu_1(z_0-z)),$$

wherein $$Ei(x) = P\int_{-\infty}^x dt\frac{e^t}{t} = \gamma + \ln|x| + \Sigma_{k=1}^\infty \frac{x^k}{kk!}$$

is the exponential integral and P denotes the principal value and $\gamma \approx 0.577$ is Euler's constant.

Similar to the previous embodiment, the primary K-escape of Cd (n=1) can be represented as:

$$P_1(E_0+\Delta_1, z_0) = \frac{P_1(E_0)}{2}(\mu_1 z_0 Ei(-\mu_1 z_0)+e^{-\mu_1 z_0}) \quad (12)$$

The primary K-escape of Te (n=2) can be represented as:

$$P_2(E_0+\Delta_2, z_0) = \frac{P_2(E_0)}{2}(\mu_2 z_0 Ei(-\mu_2 z_0)+e^{-\mu_2 z_0}) \quad (13)$$

The secondary K-escape of Te/Cd (n=3) can be defined as:

$$P_3(E_0+\Delta_3, z_0) = \quad (13)$$

$$-\frac{P_1(E_0)P_{21}\mu_1}{4}\int_0^{z_0} dz(\mu_2 z Ei(-\mu_2 z)+e^{-\mu_2 z})Ei(-\mu_1(z_0-z))-$$

$$\frac{P_1(E_0)P_{21}\mu_1}{4}\int_{z_0}^\infty dz(\mu_2 z Ei(-\mu_2 z)+e^{-\mu_2 z})Ei(\mu_1(z_0-z))$$

Upon computing the primary and secondary escape probabilities from pixel detectors, as described by the above embodiments, the measured component spectrum can be modeled based on the geometry of the detector.

Figure 3:
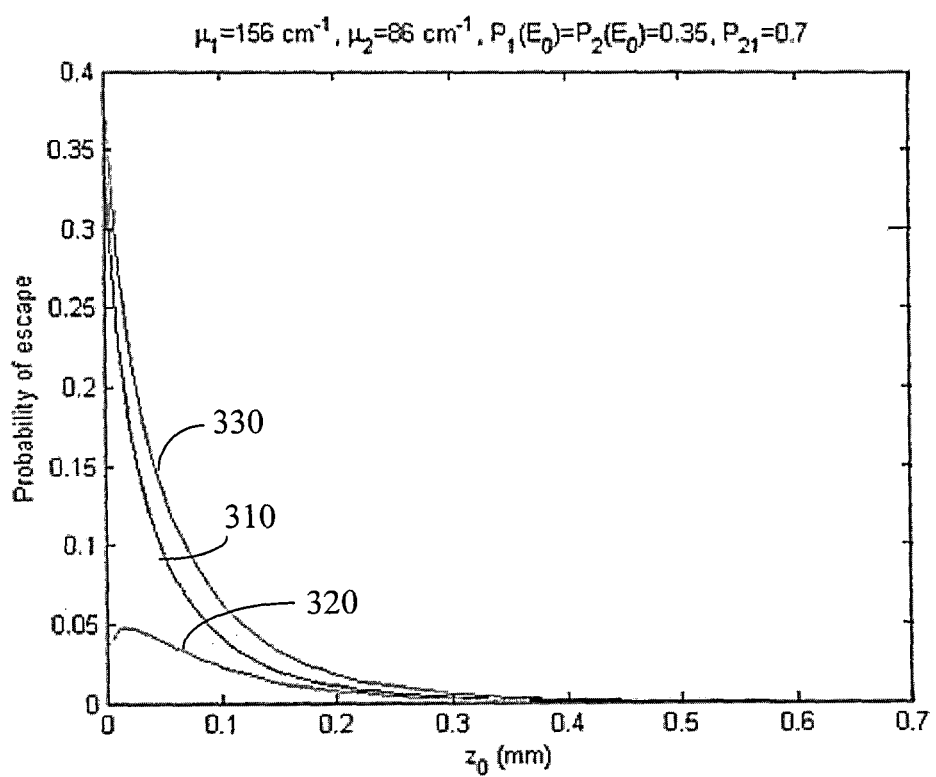
FIG. 3 depicts a graph illustrating a comparison of a primary escape and a secondary escape probability.

FIG. 3 illustrates a graph that depicts a comparison between the primary and secondary escape probabilities for varying depths within the detector at which the photoelectric interaction occurs. In FIG. 3, curve 310 represents the primary escape probability, curve 320 represents secondary escape probability, and curve 330 represents a sum of the primary and secondary escape probabilities.

It is observed that the probability of escape is higher near the surface of the detector and reduces in an exponential manner as the depth within the detector increases. Note that at smaller depths (i.e., at the surface of the detector), the angle of incidence of the incoming photon is large. Further, from FIG. 3, it is evident that the primary escape probabilities are significantly greater that the secondary escape probabilities at lower depths. This indicates that when a photoelectric interaction occurs near the surface of the detector, there is a high probability that the emitted photon escapes from the detector rather than being reabsorbed again by another detector.

Upon determining the primary escape and secondary escape probabilities, as described in the above embodiments, the measured output spectrum can be modeled based on a specific detector configuration. According to one embodiment, considering the detector configuration of FIG. 2, wherein an incident photon is absorbed by a neighboring pixel thereby causing a secondary emission, the component spectrum without pileup can be determined as follows:

$$S_0(E) = \chi_0 e^{-N\tau_d} \quad (14)$$

$$\int\int dz_0 dE_0 S_{in}(E_0)[1 - P(E_0, z_0)]e^{-\mu_{CZT}(E_0)z_0/\sin\beta}\frac{\mu_{CZT}(E_0)}{\sin\beta} +$$

$$\chi_0 e^{-N\tau_d} \sum_{m\in F(all)}\sum_n \int\int dz_0 dE_0 S_{in}(E_0 + \Delta_n)$$

$$P_n^{(m)}(E_0 + \Delta_n, z_0)e^{-\mu_{CZT}(E_0+\Delta_n)z_0}\frac{\mu_{CZT}(E_0+\Delta_n)}{\sin\beta} +$$

$$\sum_k \chi_0 e^{-N^{(k)}\tau_d} \sum_{m\in F(neighbor)}\sum_n \int\int dz_0 dE_0 S_{in}^{(k)}(E_0 + \Delta_n)$$

$$P_n^{(m)}(E_0 + \Delta_n, z_0)e^{-\mu_{CZT}(E_0+\Delta_n)z_0}\frac{\mu_{CZT}(E_0+\Delta_n)}{\sin\beta},$$

wherein the total probability of escape $P(E_0, z_0)$ is computed over all the surfaces of a given pixel. For instance, if the pixel is considered to have a cubic shape, the total probability of escape is computed over all six surfaces of the cube. Furthermore, the total probability of escape is computed over all the different ways of escape from materials having different energy levels (i.e., n=1, 2 and the like). Specifically, the total probability of escape can be defined as:

$$P(E_0, z_0) = \sum_{m\in F(all)}\sum_n P_n^{(m)}(E_0, z_0) \quad (15)$$

The term $P_n^{(m)}(E_0+\Delta_n, z_0)=P_n(E_0+\Delta_n)P_{esc}^{(m)}(\Delta_n, z_0)$, where $P_n(E_0+\Delta_n)$ is the photoelectric probability for atomic state n at photon energy $E_0+\Delta_n$. The term $P_{esc}^{(m)}(\Delta_n, z_0)$ is the escape probability of a photon with energy $\Delta_n$ generated at position $z_0$ escaping through surface m. In equation (14), the variable F(all) indicates all 6 surfaces of a pixel and the variable F(neighbor) indicates the neighboring surfaces for a given pixel. The variable k in equation (14) is summed over all neighboring detector elements of the current detector.

In equation (14), the first term (the measured component spectrum when there is no escape) is similar to that of equations (5) and (8). The second term corresponds to the energy that escapes from the sides of the pixel detector and is lost from the detector element. The third term in equation (14) corresponds to energy that escapes from the given detector and enters a neighboring detector. Note that the second and third terms in equation (14) may correspond to energy that escapes from a given surface of the pixelated detector. However, a part of the energy may be lost from the detector while another part of the energy enters the neighboring pixel detector.

Figure 4B:
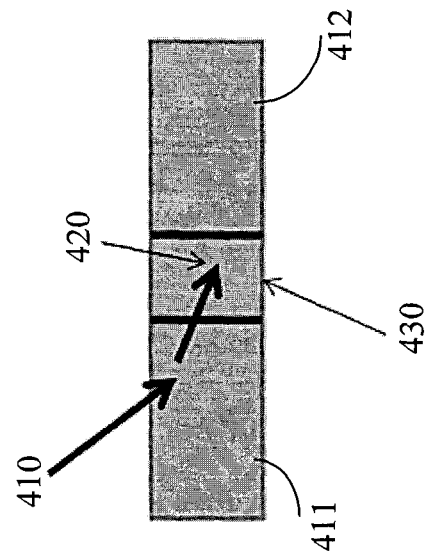
FIG. 4A illustrates a 2D pixelated detector and FIG. 4B illustrates detector pixels with an inactive zone between the pixels.
Figure 4A:
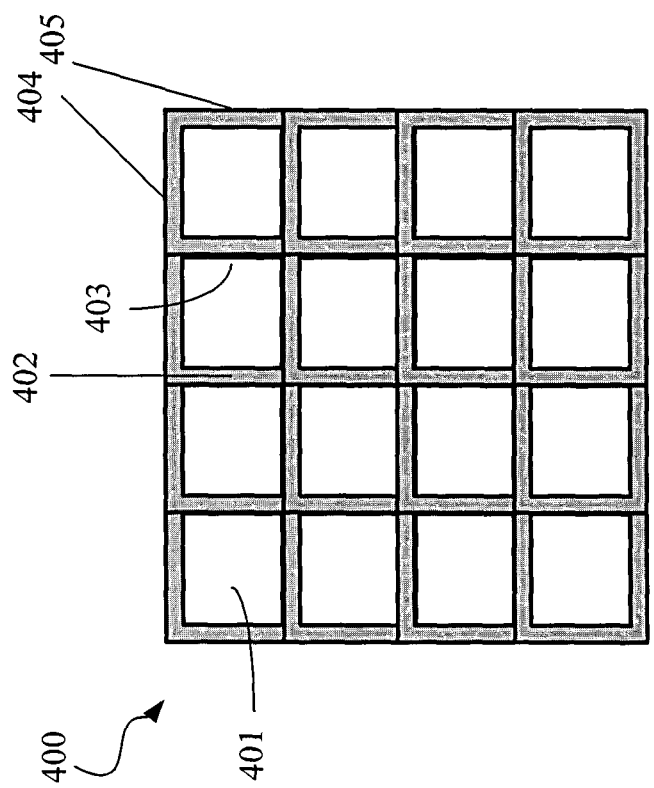

According to another embodiment, the measured component spectrum can be determined for a 2D detector array 400 shown in FIG. 4A. The detector array has a top surface 401, air side surfaces 404 and 405, an inactive zone 402, and neighboring edges 403.

The component spectrum without pile up can be represented as:

$$S_0(E) = \chi_0 e^{-N\tau_d} \quad (16)$$

$$\int\int dz_0 dE_0 S_{in}(E_0)[1 - P(E_0, z_0)]e^{-\mu_{CZT}(E_0)z_0/\sin\beta}\frac{\mu_{CZT}(E_0)}{\sin\beta} +$$

$$\chi_0 e^{-N\tau_d} \sum_{m\in F(all)}\sum_n \int\int dz_0 dE_0 S_{in}(E_0 + \Delta_n)$$

$$P_n^{(m)}(E_0 + \Delta_n, z_0)e^{-\mu_{CZT}(E_0+\Delta_n)z_0}\frac{\mu_{CZT}(E_0+\Delta_n)}{\sin\beta}$$

wherein $P(E_0, z_0) = \sum_{m\in F(all)}\sum_n P_n^{(m)}(E_0, z_0)$ and $P_n^{(m)}(E_0+\Delta_n, z_0)=P_n(E_0+\Delta_n)P_{esc}^{(m)}(\Delta_n, z_0)$, where $P_n(E_0+\Delta_n)$ is photoelectric probability for atomic state n at photon energy $E_0+\Delta_n$, $P_{esc}^{(m)}(\Delta_n, z_0)$ is the escape probability of a photon with energy $\Delta_n$ generated at position $z_0$ escaping through surface m. The parameter F(all) indicates all 6 surfaces of a given detector element and the variable F(neighbor) indicates the neighbor surfaces (sides) of the given detector.

Once the parameters (K-escape primary and secondary probabilities) have been evaluated, a model for no-pileup can be formulated based on the computed probabilities and the geometry of the photon-counting detector. Specifically, the measured component spectrum can be formulated as shown in equations (14) or (15) based on the geometry of the photon-counting detectors.

As described in prior U.S. patent application Ser. No. 13/866,695, which is incorporated herein by reference, in order to apply a CT model for spectrum correction, the parameters of the model may be analytically derived (i.e., theoretically derived) as described in the above embodiments, or may be calibrated using empirical calibration techniques. Furthermore, a combination of theoretical derivation and calibration can be used to reduce the overall computation load on the system.

Further, a response function of the no-pileup model can be determined based on the primary and secondary escape probabilities. Upon determining the response function, several algorithms can be used for spectrum correction. Specifically, algorithms such as a gradient-based method to minimize a cost function, search-based methods to find the incident spectrum in a pre-determined search domain so as to minimize a cost function, response-function based iterative methods or the like can be used for spectrum correction using the model, i.e., solving for the incident spectrum based on a measured spectrum.

Figure 5:
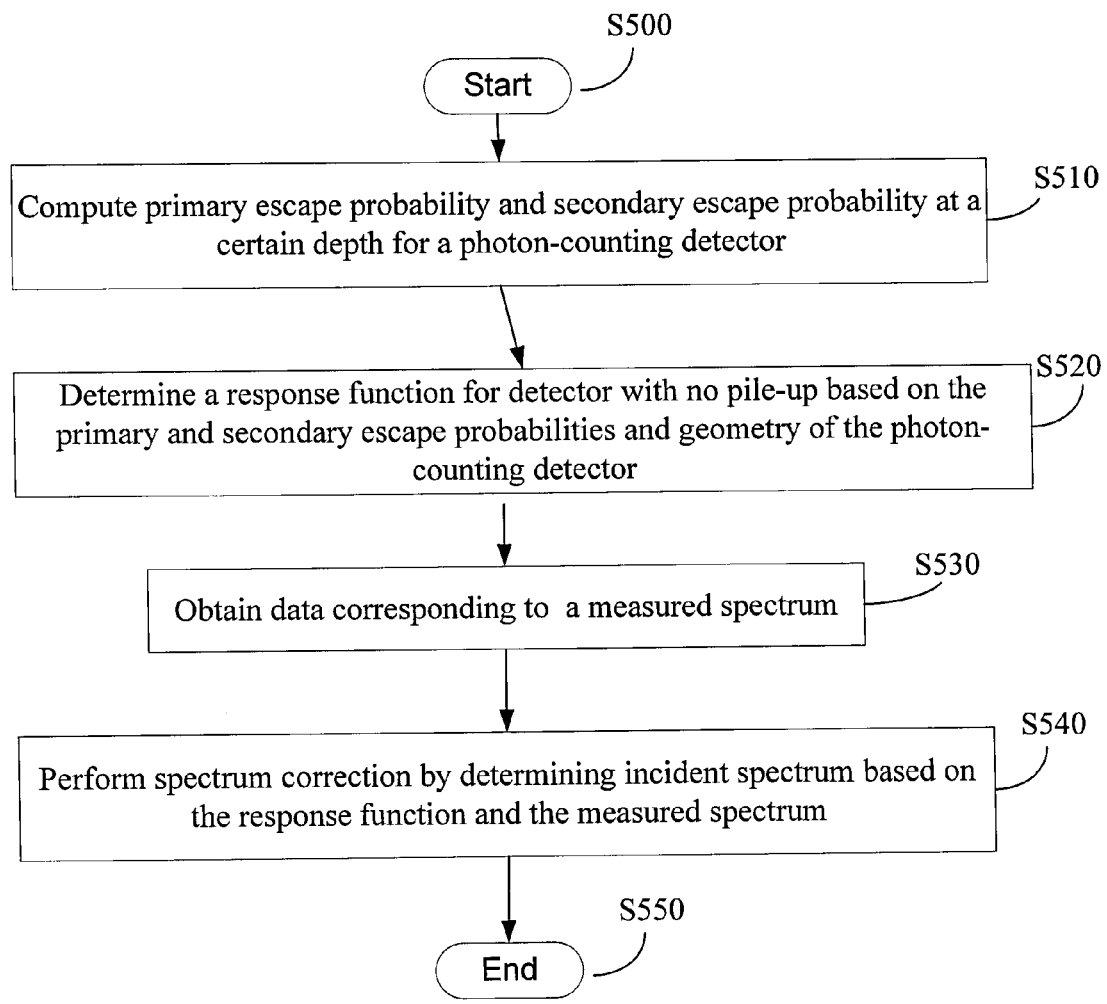
FIG. 5 is a flowchart illustrating the steps performed in spectrum correction.

FIG. 5 is a flowchart illustrating the steps performed in spectrum correction. The process starts in step S500 and proceeds to step S510.

In step S510, a primary escape probability and a second escape probability are computed in order to determine a total escape probability of a photon from a photon-counting detector upon occurrence of a photoelectric phenomenon. The primary and secondary escape probabilities can be computed as shown in equations (2) and (9).

In step S520, a response function for the photon-counting detector with no pile-up is analytically formulated based on the computed primary and secondary escape probabilities, and geometry (configuration) of the photon-counting detector. For instance, as shown in equation (14), the component spectrum is formulated by taking into account the energy that escapes from the surfaces of the detector and the amount of energy that is absorbed by a neighboring detector.

In step S530, a measured spectrum of an object is obtained.

In step S540, spectrum correction is performed by determining the incident spectrum based on the response function (analytically derived) and the measured spectrum. After performing spectrum correction the process ends in step S550.

The embodiments described herein, are in no way limiting to a particular geometry of the pixelated detector. Rather, spectrum correction can be performed on any detector geometry. For instance, spectrum correction can also be performed on a detector having the configuration as depicted in FIG. 4B. In FIG. 4B, two detectors 411 and 412 have an inactive zone 430 between them. Note that for such a configuration, neighboring side K-escape (for an incident beam 410) occurs with reabsorption (represented as 420) in the inactive zone. In this case, there is no inter-pixel distortion caused by the K-escape.

For smaller detectors, wherein the ratio of photon energy that escapes from the top surface of the detector to the energy that escapes from the sides of the detector is small, Monte Carlo simulations can be used to determine the probabilities of escape from the top surface and the sides of the detector element.

Specifically, considering a small detector that has a configuration as shown in FIG. 2, the energy that escapes into the neighboring detector element and the re-absorption probabilities can be computed using Monte Carlo simulations in order to determine the inter-detector spectrum effects. Further, for smaller detectors having an inactive zone between them, as shown in FIG. 4B, Monte Carlo simulations can be used to determine the probability of escape from the surface and sides of the detectors. Note that in a detector with such a configuration, re-absorption phenomenon occurs in the inactive zone and there is no effect on the spectrum in the neighboring detector due to the re-absorption phenomenon. Furthermore, Monte Carlo simulations can be used to determine K-escape probabilities for a small 2D pixilated detector as shown in FIG. 4A.

Figure 6:
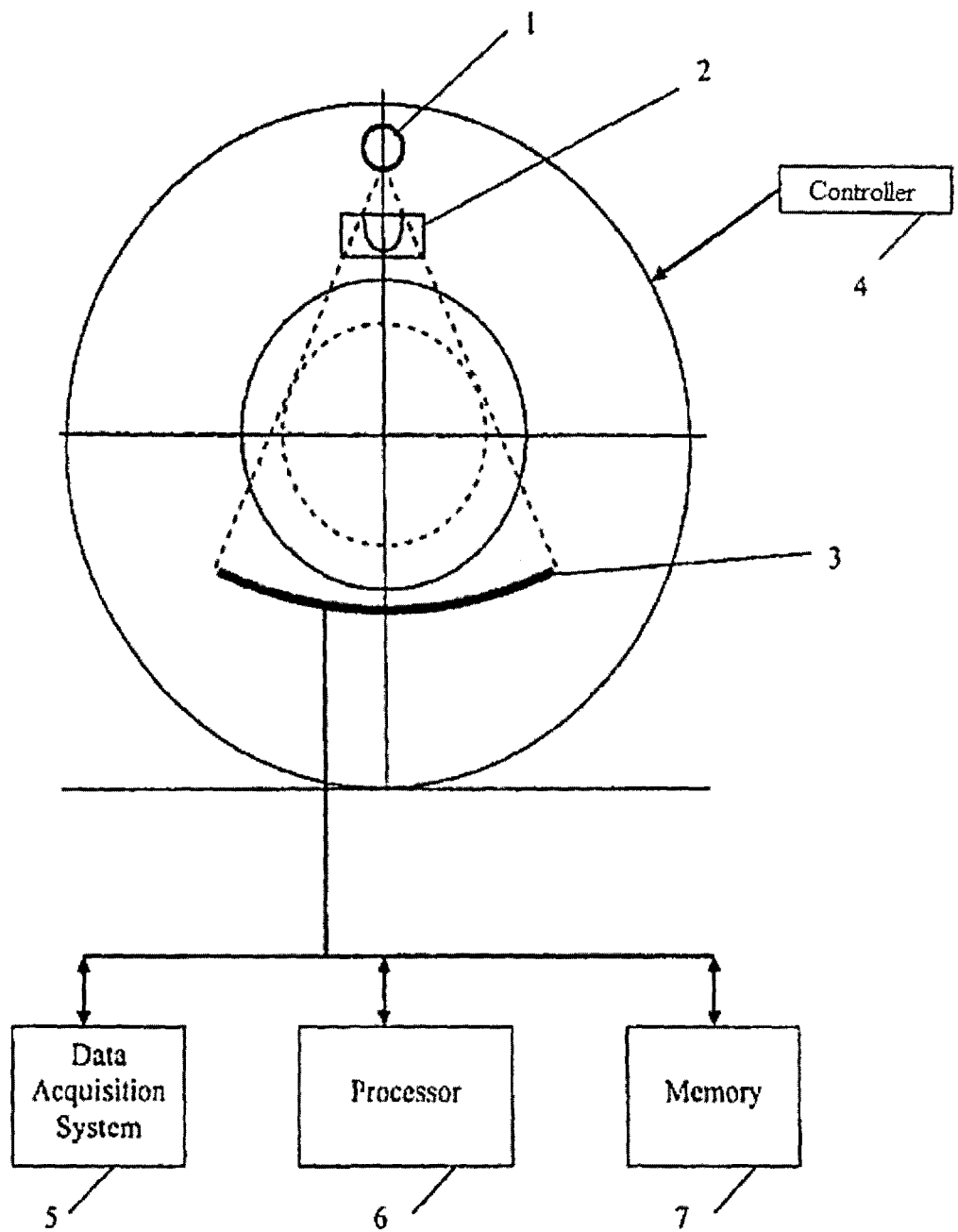
FIG. 6 and FIG. 7 illustrate a CT scanner according to the present embodiments.
Figure 7:
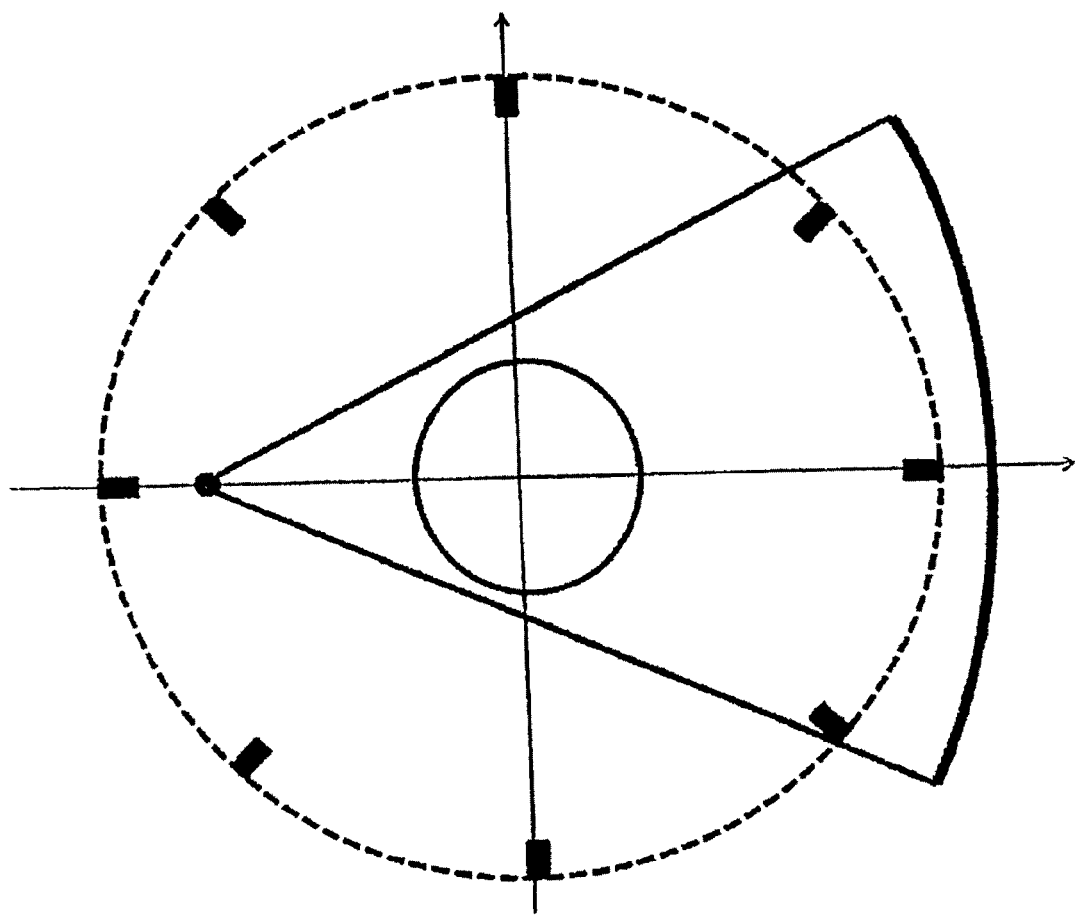

FIG. 6 illustrates the basic structure of a CT apparatus that includes the detectors described herein. The CT apparatus of FIG. 6 includes an X-ray tube 1, filters and collimators 2, and detector 3. The CT apparatus also includes, e.g., sparse fixed energy-discriminating (e.g., photon-counting) detectors, which can be arranged at a different radius from that of a third-generation detector, as shown in FIG. 7. In the detector configuration shown in FIG. 7, the photon counting detectors collect primary beams through a range of detector fan angles. The CT apparatus will also include additional mechanical and electrical components such as a gantry motor and a controller 4 to control the rotation of the gantry, control the X-ray source, and control a patient bed. The CT apparatus also includes a data acquisition system 5 and a processor 6 to generate CT images based on the projection data acquired by the data acquisition system. The processor and data acquisition system make use of a memory 7, which is configured to store, e.g., data obtained from the detector and reconstructed images.

The processor 6 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art.

The processor includes a reconstruction processor, which is configured to generate CT images from the new data. The images are stored in the memory, and/or displayed on a display. As one of ordinary skill in the art would recognize, memory can be a hard disk drive, CD-ROM drive, DVD drive, FLASH drive, RAM, ROM or any other electronic storage known in the art. The display can be implemented as an LCD display, CRT display, plasma display, OLED, LED or any other display known in the art. As such, the descriptions of the memory and the display provided herein are merely exemplary and in no way limit the scope of the present advancements.

While certain embodiments have been described, these embodiments have been presented by way of example only and are not intended to limit the scope of the inventions. Indeed the novel methods and systems described herein may be embodied in a variety of other forms. Furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A computed-tomography (CT) apparatus, the apparatus comprising:
   an X-ray tube configured to radiate X-rays toward an object;
   a photon-counting detector configured to capture incident X-ray photons emitted from the X-ray tube; and
   processing circuitry configured to
      compute a plurality of primary K-escape probabilities and a plurality of secondary K-escape probabilities for the photon-counting detector, wherein computing the primary K-escape probabilities includes computing, for a given energy of an incident photon and a given depth at which a photoelectric interaction occurs, a sum, over a plurality of escape types, of a product of (1) a probability of a K-edge photon being emitted for the given energy when the photoelectric interaction has occurred, and (2) an integral over a solid angle that depends on the given depth;
      determine a response function for the photon-counting detector based on the computed primary and secondary K-escape probabilities and a geometry of the photon counting detector;
      obtain, from the photon-counting detector, a measured output spectrum corresponding to the incident X-ray photons; and
      generate a CT image using the response function and the measured output spectrum.

2. The CT apparatus of claim 1, wherein the response function includes a first energy portion that contributes to the measured spectrum and is based on a total probability of no escape from the photon-counting detector, and a second energy portion that contributes to the measured spectrum and is based on the plurality of primary and secondary K-escape probabilities from the photon-counting detector.

3. The CT apparatus of claim 2, wherein the second energy portion further includes a third energy portion that corresponds to energy that escapes from a plurality of surfaces of the photon-counting detector and is lost from the photon-counting detector, and a fourth energy portion that exits the photon-counting detector and enters a neighboring photon-counting detector.

4. The CT apparatus of claim 1, wherein the primary K-escape probabilities and the secondary K-escape probabilities depend on a depth within the photon-counting detector at which the photoelectric interaction occurs.

5. The CT apparatus of claim 4, wherein the depth within the photon-counting detector at which the photoelectric interaction occurs corresponds to an incident angle formed between an incident photon that impinges the photon-counting detector and a normal to the surface of the photon-counting detector.

6. The CT apparatus of claim 1, wherein the measured output spectrum is related to an incident spectrum by the response function.

7. A method for a spectral computed-tomography (CT) scanner, the scanner including an X-ray tube to radiate X-rays toward an object and a photon-counting detector to capture incident X-ray photons emitted from the X-ray tube, the method comprising:
   computing a plurality of primary K-escape probabilities and a plurality of secondary K-escape probabilities for the photon-counting detector, wherein computing the primary K-escape probabilities includes computing, for a given energy of an incident photon and a given depth at which a photoelectric interaction occurs, a sum, over a plurality of escape types, of a product of (1) a probability of a K-edge photon being emitted for the given energy when the photoelectric interaction has occurred, and (2) an integral over a solid angle that depends on the given depth;
   determining a response function for the photon-counting detector based on the computed primary and secondary K-escape probabilities and a geometry of the photon-counting detector;
   obtaining, from the photon-counting detector, a measured output spectrum corresponding to the incident X-ray photons; and
   generating a CT image using the response function and the measured output spectrum.

8. The method of claim 7, wherein the response function includes a first energy portion that contributes to the measured spectrum and is based on a total probability of no escape from the photon-counting detector, and a second energy portion that contributes to the measured spectrum and is based on the plurality of primary and secondary K-escape probabilities from the photon-counting detector.

9. The method of claim 8, wherein the total probability of no escape is based on a sum of the primary K-escape probabilities and the secondary K-escape probabilities.

10. The method of claim 8, wherein the second energy portion further includes a third energy portion that corresponds to energy that escapes from a plurality of surfaces of the photon-counting detector and is lost from the photon-counting detector, and a fourth energy portion that exits the photon-counting detector and enters a neighboring photon-counting detector.

11. The method of claim 7, wherein the measured output spectrum is related to an incident spectrum by the response function.

12. The method of claim 7, wherein the primary K-escape probabilities and the secondary K-escape probabilities depend on a depth within the photon-counting detector at which the photoelectric interaction occurs.

13. The method of claim 12, wherein each primary K-escape probability is greater than a corresponding secondary K-escape probability for the depth at which the photoelectric interaction occurred.

14. The method of claim 12, wherein the primary K-escape and the secondary K-escape probabilities reduce exponentially with increasing depths within the photon-counting detector at which the photoelectric interaction occurs.

15. The method of claim 13, wherein the depth within the photon-counting detector at which the photoelectric interaction occurs corresponds to an incident angle formed between an incident photon that impinges the photon-counting detector and a normal to the surface of the photon-counting detector.

16. The method of claim 15, wherein each probability of primary K-escape increases with increasing angle of incidence.

17. A non-transitory computer readable medium having stored thereon a program that when executed by a computer, causes the computer to perform a method for a spectral computed-tomography (CT) scanner including an X-ray tube to radiate X-rays toward an object and a photon-counting detector to capture incident X-ray photons emitted from the X-ray tube, the method comprising:
   computing a plurality of primary K-escape probabilities and a plurality of secondary K-escape probabilities for the photon-counting detector, wherein computing the primary K-escape probabilities includes computing, for a given energy of an incident photon and a given depth at which a photoelectric interaction occurs, a sum, over a plurality of escape types, of a product of (1) a probability of a K-edge photon being emitted for the given energy when the photoelectric interaction has occurred, and (2) an integral over a solid angle that depends on the given depth;
   determining a response function for the photon-counting detector based on the computed primary and secondary K-escape probabilities and a geometry of the photon-counting detector;
   obtaining, from the photon-counting detector, a measured output spectrum corresponding to the incident X-ray photons; and
   generating a CT image using the response function and the measured output spectrum.

* * * * *